(12) United States Patent
Schaefer et al.

(10) Patent No.: US 6,693,120 B1
(45) Date of Patent: Feb. 17, 2004

(54) SPRAY DRYING OF THROMBIN INHIBITORS

(75) Inventors: Bernd Schaefer, Dierbach (DE); Guido Harms, Limburgerhof (DE); Hermann Ascherl, Dirmstein (DE); Georg Arnold Krei, Altrip (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/959,786

(22) PCT Filed: May 3, 2000

(86) PCT No.: PCT/EP00/03965

§ 371 (c)(1),
(2), (4) Date: Jul. 2, 2002

(87) PCT Pub. No.: WO00/68254

PCT Pub. Date: Nov. 16, 2000

(30) Foreign Application Priority Data

May 10, 1999 (DE) .......................................... 199 21 346

(51) Int. Cl.$^7$ .................. A61K 31/4439; C07D 401/12
(52) U.S. Cl. ..................... 514/343; 514/343; 546/279.1
(58) Field of Search .......................... 514/19, 970, 973, 514/769, 788; 546/279, 279.1

(56) References Cited

U.S. PATENT DOCUMENTS

| | | | | |
|---|---|---|---|---|
| 4,861,591 A | | 8/1989 | Weierstall et al. ........... | 424/690 |
| 5,627,179 A | | 5/1997 | Jaeger et al. ................ | 514/222 |
| 6,030,972 A | | 2/2000 | Böhm et al. ................. | 514/257 |
| 6,407,067 B1 | * | 6/2002 | Schafer ....................... | 514/19 |

FOREIGN PATENT DOCUMENTS

| | | |
|---|---|---|
| DE | 261 162 | 10/1988 |
| EP | 0 040 472 | 11/1981 |
| FR | 2097079 | 3/1972 |
| GB | 956944 | 4/1964 |
| WO | WO 94/26727 | 11/1994 |
| WO | WO 96/25426 | 8/1996 |

* cited by examiner

Primary Examiner—Alan L. Rotman
Assistant Examiner—Janet L Coppins
(74) Attorney, Agent, or Firm—Wood, Phillips, Katz, Clark & Mortimer

(57) ABSTRACT

The invention relates to a process for preparing constant-weight thrombin inhibitors of the formula I

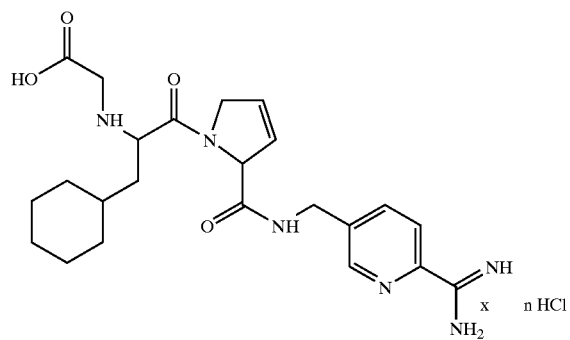

(I)

where n is 0, 1, 2, and tautomers thereof,
wherein an aqueous solution of the active substance is spray dried.

7 Claims, No Drawings

SPRAY DRYING OF THROMBIN INHIBITORS

The present application is a 371 of PCT/EP 00/03965, filed May 3, 2000.

The invention relates to processes for preparing constant-weight thrombin inhibitors, specifically the spray drying of such inhibitors. The invention additionally relates to novel salts of thrombin inhibitors, to drugs comprising the latter and to the use of these salts for producing medicines with antithrombotic effect.

The invention specifically relates to novel salts of the general formula I, the preparation and use thereof, where formula I has the following meaning:

(I)

where n is 0, 1, 2, and tautomers thereof.

The R configuration of cyclohexylalanine and the S configuration of dehydroproline are preferred.

The preparation of the thrombin inhibitor I as acetate is described in WO 96/25426 (Example 93, page 128). On isolation of the active substance on an RP column operated with acetic acid buffer (see PCT application page 65, lines 25/26), the product is obtained in the form of the acetic acid salt, irrespective of its previous history. The acetic acid salt is hygroscopic and forms a number of byproducts during storage.

Defined compounds of the formula I are obtained by titrating acidic solutions of the active substance with aqueous ammonia. During this, the betaine of the active substance precipitates and can be obtained in pure form by filtration or centrifugation and drying. The hydrochlorides of the general formula I are obtained by adding stoichiometric amounts of HCl to the betaine. Suitable solvents are water, $C_1$–$C_6$-alcohols, $C_1$–$C_6$-ethers, $C_1$–$C_6$-esters, toluene, xylenes, DMF, DMSO, THF. The product is isolated by filtration or centrifugation and drying.

The active substance is prone to irreversible adsorption of organic solvents. organic solvent residues are disadvantageous for pharmaceutical preparations. Isolation from water would be an attractive process. This does not result in constant-weight products because the active substance is highly hygroscopic. The extent of the hygroscopicity depends on the relative humidity.

To determine the hygroscopicity, samples of the dry active substance are stored in desiccators in which a constant humidity has been set by saturated salt solutions, at constant temperature. The weight change is determined by weighing at intervals of a few days. The weight gain is determined by the following formula:

$$\text{weight gain} = \frac{\text{(weight after adsorption)} - \text{dry weight}}{\text{dry weight}} \times 100$$

By way of example the weight gain is shown for the example of vacuum-ried active substance with n=1 in Table 1 below:

TABLE 1

| days | 45% R.H. | 65% R.H. | 75% R.H. | 86% R.H. | 93% R.H. |
|------|----------|----------|----------|----------|----------|
| 0    | 0        | 0        | 0        | 0        | 0        |
| 3    | 0.28     | 3.50     | 7.60     | 15.51    | 19.73    |
| 6    | 0.31     | 3.86     | 9.31     | 20.23    | 20.34    |
| 9    | 0.26     | 3.59     | 7.98     | 16.66    | 18.97    |
| 14   | 0.23     | 3.54     | 7.84     | 16.61    | 19.11    |
| 21   | 0.26     | 3.45     | 7.86     | 16.14    | 18.78    |

The setting up of a process chain in which the active substance is at constant humidity from production to storage to pharmaceutical processing is extremely complicated.

It is an object of the present invention to prepare an easily handled, constant-weight active substance. It has been found, surprisingly, that on spray drying of active substance I, in contrast to all other drying techniques in vacuo, a constant residual moisture content can be set, and it thus has a constant weight during further processing.

The resulting amorphous form is moreover of pharmacological interest because of the effect of the crystallinity on the bioavailability.

The aqueous solution of the active substance to be dried is atomized by means of a two-component nozzle. A gas flowing cocurrently, preferably nitrogen, dries the dispersed drops to amorphous solid particles. These solid particles are normally removed in a cyclone. The off-gas is filtered and passed to a scrubbing tower.

The concentration of the solution to be dried is in the range from 5 to 40% by weight, preferably in the range from 15 to 25% by weight.

The gas inlet temperature is in the range from 80 to 150° C., preferably in the range from 110 to 130° C.

The gas outlet temperature is in the range from 30 to 70° C., preferably in the range from 50 to 60° C.

The pressure of the atomizing gas is in the range from 1.1 to 10 bar, preferably in the range from 2 to 5 bar.

The products prepared in this way are compact, and pharmaceutical processing thereof is easy.

A product prepared in this way can be handled in the open air without a rapid change in its weight.

The spray-dried products of the general formula I show a weight gain of less than 1% after several days even with a relative humidity of 75% after spray drying.

The vacuum-dried and freeze-dried products of the general formula I show a weight gain of more than 6% at 75% relative humidity.

In addition, comparison of the storage stability of the salts I according to the invention with fumarate and acetate salts surprisingly reveals that the active substances according to the invention are more stable on storage than are the corresponding salts of organic acids.

TABLE 2

Storage at 70° C., 1 bar in an open vessel. Data are
active substance content based on initial active
substance content in the open vessel in HPLC % areas

| Days | Betaine (n = 0) | Betaine x HCl | Betaine x 2HCl | Betaine x acetate | Betaine x fumarate |
|---|---|---|---|---|---|
| 0 | 100 | 100 | 100 | 100 | 100 |
| 7 | 92.5 | 98.5 | 99.7 | 92.6 | 87.9 |
| 14 | 88.6 | 97.5 | 99.7 | 87.1 | 87.1 |

TABLE 3

HPLC content of the active substance in % areas
active substance formula I n = 1

|  | spray dried | vacuum dried (60° C./12 h) |
|---|---|---|
| active substance | 98.5% | 97.8% |
| byproducts | no additional byproducts over 0.1% | additional byproducts with contents of more than 0.1% |

The compounds of the formula I are thrombin inhibitors and can be employed for the following indications:
diseases whose pathomechanism is based directly or indirectly on the proteolytic effect of thrombin,
diseases whose pathomechanism is based on the thrombin-dependent activation of receptors and signal transduction,
diseases associated with stimulation [for example by PAI-1, PDGF (platelet derived growth factor), P-selectin, ICAM-1, tissue factor] or inhibition (for example NO synthesis in smooth muscle cells) of the expression of genes in body cells,
diseases based on the mitogenic effect of thrombin,
diseases based on a thrombin-dependent change in the contractility and permeability of epithelial cells (for example vascular endothelial cells).
thrombin-dependent thromboembolic events such as deep vein thrombosis, pulmonary embolism, myocardial or cerebral infarction, atrial fibrillation, bypass occlusion,
disseminated intravascular coagulation (DIC),
reocclusion and for reducing the reperfusion time on comedication with thrombolytics such as streptokinase, urokinase, prourokinase, t-PA, APSAC, plasminogen activators from the salivary glands of animals, and the recombinant and mutated forms of all these substances,
the occurrence of early reocclusion and late restenosis after PTCA,
thrombin-dependent proliferation of smooth muscle cells,
accumulation of active thrombin in the CNS (for example in Alzheimer's disease),
tumor growth, and to prevent the adhesion and metastasis of tumor cells.

The novel compounds can be used in particular for the therapy and prophylaxis of thrombin-dependent thromboembolic events such as deep vein thrombosis, pulmonary embolisms, myocardial or cerebral infarctions and unstable angina, also for the therapy of disseminated intravascular coagulation (DIC). They are further suitable for combination therapy with thrombolytics such as streptokinase, urokinase, prourokinase, t-PA, APSAC and other plasminogen activators for reducing the reperfusion time and extending the reocclusion time.

Further preferred areas of use are the prevention of thrombin-dependent early reocclusion and late restenosis after percutaneous transluminal coronary angioplasty, the prevention of thrombin-induced proliferation of smooth muscle cells, the prevention of the accumulation of active thrombin in the CNS (for example in Alzheimer's disease), the control of tumors and the prevention of mechanisms which lead to adhesion and metastasis of tumor cells.

The novel compounds can also be used for coating artificial surfaces such as hemodialysis membranes and the tubing systems and lines necessary therefor, and oxygenators for an extravascular circulation, stents and heart valves.

The novel compounds can also be employed for diseases whose pathomechanism is based directly or indirectly on the proteolytic effect of kininogenases, especially kallikrein, for example for inflammatory diseases such as asthma, pancreatitis, rhinitis, arthritis, urticaria and other internal inflammatory diseases.

The compounds according to the invention can be administered orally or parenterally (subcutaneously, intravenously, intramuscularly, intraperitoneally, rectally) in a conventional way. Administration can also take place with vapors or sprays through the nasopharyngeal space. The compounds can in particular be given orally.

The dosage depends on the age, condition and weight of the patient and on the mode of administration. The daily dose of active substance per person is usually between about 10 and 2000 mg on oral administration and between about 1 and 200 mg on parenteral administration. This dose can be given in 2 to 4 single doses or once a day as depot form.

The novel compounds can be used in conventional solid or liquid pharmaceutical forms, for example as uncoated or (film-)coated tablets, capsules, powders, granules, suppositories, solutions, ointments, creams or sprays. These are produced in a conventional way. The active substances can for this purpose be processed with conventional pharmaceutical excipients such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain the active substance in an amount of 0.1 to 99% by weight.

EXAMPLES

1st Example

N-((Hydroxycarbonyl)methylene)-(R)-cyclohexylalanyl-(S)-3,4-dehydroproline 6-Amidino-3-Picoli-nylamide (Betaine)

90 g (0.116 mol) of the compound N-boc-N-((t-butoxycarbonyl)methylene)-(R)-cyclohexylalanyl-(S)-3,4-dehydroproline 6-amidino-3-picolinylamide N-acetyl-(S)-cysteinate, which is described in Example 3 of WO 98/09950, 360 g of water and 44.56 g (38% strength, 0.464 mol) of hydrochloric acid were heated at 65° C. for 2h. Cooling to room temperature was followed by extraction once with ethyl acetate, and the phases were separated and adjusted to pH 8.2 with 105 g of a 25% aqueous ammonia solution. This precipitated the product. It was then stirred for one hour, filtered off with suction, washed with ice-water and then dried in a vacuum oven. 41.66 g (0.091 mol, 79%) of N-((hydroxycarbonyl)methylene)-(R)-cyclohexylalanyl-(S)-3,4-dehydroproline 6-amidino-3-picolinylamide were obtained in the form of a colorless solid.

2nd Example

N-((Hydroxycarbonyl)methylene)-(R)-cyclohexylalanyl-(S)-3,4-dehydroproline 6-Amidino-3-picolinylamide Hydrochloride 29.4 kg (88% pure, 57 mol) of N-((hydroxycarbonyl)methylene)-(R)-cyclohexylalanyl-(S)-3,4-dehydroproline 6-amidino-3-picolinylamide in 100 kg of water were mixed with 5.45 kg (38% strength, 57 mol) of hydrochloric acid, were clarified by filtration and spray dried. 27.1 kg (93% pure, 51 mol, 89%) of N-((hydroxycarbonyl)methylene)-(R)-cyclohexylalanyl-(S)-3,4-dehydroproline 6-amidino-3-picolinylamide hydrochloride were obtained in the form of a colorless powder.

3rd Example

N-((Hydroxycarbonyl)methylen)-(R)-cyclohexylalanyl-(S)-3,4-dehydroproline 6-Amidino-3-picolinylamide Dihydrochloride 3.2 g (6.1 mmol) of N-((hydroxycarbonyl)methylene)-(R)-cyclohexylalanyl-(S)-3,4-dehydroproline 6-amidino-3-picolinylamide hydrochloride were introduced into 40 ml of water and, after addition of 6.1 g of 1 molar hydrochloric acid, the solution was freeze dried. 3.25 g (6.1 mol) 100%) of N-((hydroxycarbonyl)methylene)-(R)-cyclohexylalanyl-(S)-3,4-dehydroproline 6-amidino-3-picolinylamide dihydrochloride were obtained in the form of a colorless powder.

We claim:

1. A process for preparing a compound of the formula I

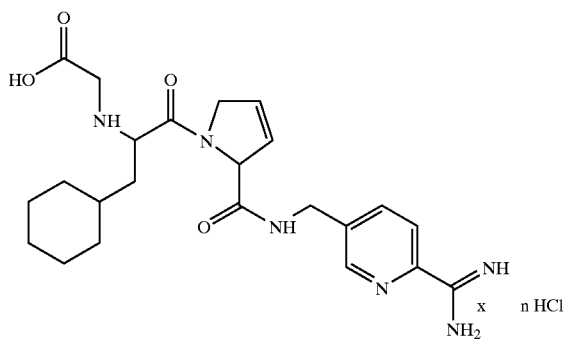

(I)

where n is 0, 1, 2,
comprising spray drying an aqueous solution of the compound.

2. A process as claimed in claim 1, wherein the concentration of the solution to be dried is in the range between 5 and 40% by weight.

3. A process as claimed in claim 1, wherein the gas inlet is in the range between 30° C. and 70° C.

4. A compound of the formula I

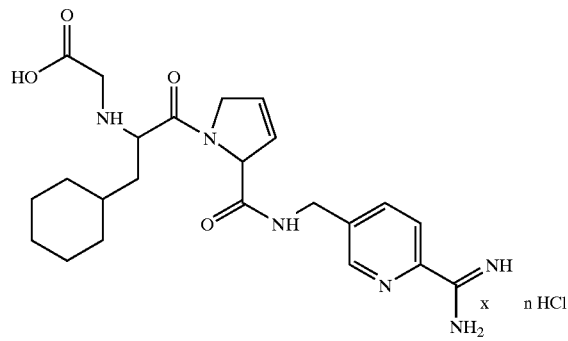

(I)

where n is 0, 1, 2.

5. A compound as claimed in claim 4 in amorphous form.

6. A drug composition comprising a compound of claim 4 in addition to pharmaceutically acceptable carriers and excipients.

7. A method of treating a patient to treat a disease selected from the group consisting of diseases whose pathomechanism is based directly or indirectly on the proteolytic effect of thrombin, diseases whose pathomechanism is based on the thrombin-dependent activation of receptors and signal transduction, diseases associated with stimulation or inhibition of the expression of genes in body cells, diseases based on the mitogenic effect of thrombin, diseases based on a thrombin-dependent change in the contractility and permeability of epithelial cells, thrombin-dependent thromboembolic events, disseminated intravascular coagulation, reocclusion and for reducing the reperfusion time on comedication with thrombolytics, the occurrence of early reocclusion and late restenosis after PTCA, thrombin-dependent proliferation of smooth muscle cells, and accumulation of active thrombin in the CNS, comprising administering to said patient an effective amount of a compound as claimed in claim 4.

* * * * *